United States Patent
Sawanoi et al.

(10) Patent No.: US 7,367,952 B2
(45) Date of Patent: May 6, 2008

(54) ELECTRONIC BLOOD PRESSURE MONITOR AND BLOOD PRESSURE MEASURING SYSTEM

(75) Inventors: Yukiya Sawanoi, Nara (JP); Hiroya Nakanishi, Kyoto (JP); Takahide Tanaka, Otsu (JP); Osamu Shirasaki, Amagasaki (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 191 days.

(21) Appl. No.: 11/298,509

(22) Filed: Dec. 12, 2005

(65) Prior Publication Data

US 2006/0142663 A1 Jun. 29, 2006

(30) Foreign Application Priority Data

Dec. 10, 2004 (JP) ............................. 2004-358815

(51) Int. Cl.
 *A61B 5/02* (2006.01)
(52) U.S. Cl. ....................................... 600/490; 600/495
(58) Field of Classification Search ................ 600/481, 600/483, 485, 490–503, 300, 301
 See application file for complete search history.

(56) References Cited

U.S. PATENT DOCUMENTS

| | | | | |
|---|---|---|---|---|
| 4,566,463 A * | 1/1986 | Taniguchi et al. | .......... | 600/495 |
| 5,649,536 A * | 7/1997 | Ogura et al. | ................ | 600/493 |
| 6,699,195 B2 * | 3/2004 | Nakazawa et al. | .......... | 600/485 |
| 7,018,335 B2 * | 3/2006 | Kario et al. | ................ | 600/485 |
| 7,172,556 B2 * | 2/2007 | Chen et al. | .................. | 600/490 |
| 7,175,600 B2 * | 2/2007 | Chen et al. | .................. | 600/490 |
| 2004/0176692 A1 | 9/2004 | Kario et al. | | |

FOREIGN PATENT DOCUMENTS

| EP | 0-423-553 A1 | 4/1991 |
|---|---|---|
| JP | 3070676 U | 8/2000 |

(Continued)

OTHER PUBLICATIONS

Verdecchia, Paolo et al. (2004). "Validation of the A&D UA-774 (UA-767Plus) Device for Self-Measurement of Blood Pressure," *Blood Pressure Monitoring* 9(4); 225-229.

(Continued)

*Primary Examiner*—Charles A. Marmor, II
*Assistant Examiner*—Navin Natnithithadha
(74) *Attorney, Agent, or Firm*—Morrison & Foerster LLP

(57) ABSTRACT

When a predetermined condition for measurement is selected from a plurality of conditions for measurement by operating one of measurement switches before measuring the blood pressure, a pressure begins to be applied to a bladder in response to the selection and the measurement of the blood pressure starts. The measured data of the blood pressure and the selected condition for measurement are linked to each other and stored in a memory. Because the measurement of the blood pressure starts upon selection of the predetermined condition by operating one of the measurement switches, one operation can serve both as switching to instruct the starting of the measurement and selecting the predetermined condition for measurement. Thus, an additional operation for inputting a condition for measurement is not necessary, and this makes it possible to prevent forgetting to input or incorrectly inputting a condition for measurement from occurring.

16 Claims, 9 Drawing Sheets

FOREIGN PATENT DOCUMENTS

| | | |
|---|---|---|
| JP | 2002-272686 A | 9/2002 |
| JP | 2004-261452 A | 9/2004 |
| RU | 2 158 107 | 10/2000 |
| TW | 396033 B | 7/2000 |
| WO | WO-2005/039408 A1 | 5/2005 |

OTHER PUBLICATIONS

Taiwanese Office Action dated Nov. 16, 2006, directed at counterpart TW application No. 094143305.

Russian Official Decision on Grant dated Apr. 11, 2007, directed to counterpart RU application No. 2005138459.

"Digital Blood Pressure Monitor UA-774" dated Feb. 17, 2004, retrieved from: http://www.aandd.jp/products/medical/consumer/catalog_pdf/ua774_ca.pdf; 1 page.

European Office Action mailed Aug. 14, 2007, directed to counterpart European Patent Application No. 05 026 651.9, 5 pages.

* cited by examiner

ELECTRONIC BLOOD PRESSURE MONITOR AND BLOOD PRESSURE MEASURING SYSTEM

BACKGROUND OF THE INVENTION

1. Field of the Invention

This invention relates to an electronic blood pressure monitor and a blood pressure measuring system, and in particular, to an electronic blood pressure monitor which can measure and record information specifically on cardiovascular risk, as well as a blood pressure measuring system.

2. Description of the Background Art

Blood pressure is a barometer for analyzing cardiac function, and risk analysis on the basis of blood pressure is effective for preventing cardiovascular system diseases, such as, for example, cerebral strokes, heart failure and myocardial infarction. For example, there is a cause and effect relationship between the surge in blood pressure that occurs between one hour and one and a half hours after waking up, which is referred to as morning surge, and cerebral stroke, and it is necessary to grasp the reciprocal relation between changes in blood pressure and health, for risk analysis of cardiovascular system diseases. As described above, blood pressure changes on the basis of individual physical activities, response to stress and reaction of the cardiovascular system to patterns of behavior, and in addition, there is a fluctuation rhythm during the course of the day, such that blood pressure drops during sleep and increases before or after waking up.

Focusing on the factors relating to the above described fluctuation in blood pressure, the applicant has proposed the blood pressure monitor that is described in Japanese Patent Laying-Open No. 2004-261452. This blood pressure monitor links the measured value of blood pressure to the information on measured time and measurement conditions, and stores these, and thus, the average values of blood pressure, which are measured within particular time slots, such as a morning time slot and an evening time slot, are respectively calculated, and the risk value is calculated and displayed on the basis of these calculation results. In this blood pressure monitor, information on the measured time is taken from the time gained through a clock function that is provided in the blood pressure monitor, and the measured values are linked to the gained information on measured time and automatically sorted and stored.

In addition, focusing on the factors relating to fluctuation, which are the same as the above, that is to say, the fact that the physiological and psychological state of the patient affects the measurement of the blood pressure when the blood pressure is measured, the blood pressure monitor that is described in Japanese Utility Model Registration No. 3070676 has been proposed. When the patient turns on the power ON this blood pressure monitor and operates the startup key so as to start the measurement of blood pressure, the results of the measurement of blood pressure are displayed, and then, the patient can operate a selection key for the state at the time of measurement (drunk, tinnitus, immediately after waking up, after exercising, after taking a bath), so that the measured value and the selected state are linked to each other and stored in a memory.

In the case where a measured value is linked to information on the measured time and stored in the blood pressure monitors of Japanese Patent Laying-Open 2004-261452 and Japanese Utility Model Registration No. 3070676, incorrect information on the measured time is linked to the measured value when the setting of the clock in the blood pressure monitor is incorrect. In addition, problems remain, such that the risk value is calculated on the basis of the time slot when blood pressure is measured, even in the case of a person such as a shift worker whose life cycle, including waking time and sleeping time, is different from ordinary people, and therefore, the risk value deviates from the risk value that is calculated from the true measured values after waking up and before sleeping.

In addition, the conditions for measurement are inputted for every measurement, by operating condition input switches provided in the blood pressure monitor. Therefore, the condition input switches must be operated for every measurement, making switching operation troublesome. In addition, problems remain, such that the correct risk value is not calculated when incorrect conditions for measurement are linked to the measured values because of the user forgetting to operate the condition input switches.

SUMMARY OF THE INVENTION

An object of this invention is to provide an electronic blood pressure monitor which makes it possible to link blood pressure data to the conditions for measurement with higher precision, as well as a blood pressure measuring system.

In order to achieve the above described object, an electronic blood pressure monitor according to one aspect of this invention is provided with: a blood pressure measuring portion having a cuff that is attached to the part where blood pressure is measured, a pressurizing and depressurizing portion for adjusting pressure that is applied to the cuff, a pressure detecting portion for detecting pressure within the cuff that is adjusted by the pressurizing and depressurizing portion, and a blood pressure calculating portion for calculating blood pressure on the basis of the pressure that is detected by the pressure detecting portion; a memory portion for storing data on blood pressure that is outputted from the blood pressure calculating portion; and a display portion for displaying at least the data on blood pressure, and in addition, is provided with:

a selection portion for selecting predetermined conditions for measurement from among a number of types of conditions for measurement before the start of measurement of blood pressure by the blood pressure measuring portion;

a control portion for starting measurement of blood pressure by the blood pressure measuring portion; and a data storing portion for linking data on blood pressure that has been outputted from the blood pressure calculating portion to the predetermined conditions for measurement that have been selected by the above described selection portion and storing the data on blood pressure and the predetermined conditions for measurement in the memory portion.

As described above, when predetermined conditions for measurement are selected by the selection portion, measurement of blood pressure is started, and the data on blood pressure that has been gained through measurement is linked to the selected predetermined conditions for measurement and stored in the memory portion, and therefore, a separate operation for inputting the conditions for measurement can be omitted.

Preferably, the selection portion is also used as an operation portion which is externally operated for instructing the start of measurement, and therefore, the configuration of the apparatus which is used both as the selection portion of the conditions for measurement and the measurement start instructing portion can be simplified.

Preferably, the operation portion has a number of switches to which the number of types of conditions for measurement are respectively made to correspond. Thus, in response to the operation of any of the number of switches, the type of conditions for measurement that is made to correspond to this switch is selected as the above described predetermined conditions for measurement. In addition, the number of types of conditions for measurement include conditions for measurement which indicate, respectively, measurement of blood pressure "after waking up" and "before sleeping."

Accordingly, conditions for measurement which are appropriate for the lifecycle (such as shift work) of individual patients can be selected.

Preferably, the number of types of conditions for measurement include conditions for measurement which indicate, respectively, measurement of blood pressure "before taking medicine," "after taking medicine," "before exercising" and "after exercising."

Preferably, the data storing portion pairs the selected predetermined conditions for measurement and the data on blood pressure for each measurement of blood pressure and stores the pair in the memory portion.

Preferably, the memory portion is provided with a memory region for each of the number of types of conditions for measurement. Thus the data storing portion stores data on blood pressure in the memory region that corresponds to the selected predetermined conditions for measurement for each measurement of blood pressure.

Preferably, a portion for calculating an evaluation amount on the basis of the mutual relationship between a group of data on blood pressure that includes at least one piece of data on blood pressure that has been measured under the same conditions for measurement, which are stored in the memory portion, and a group of data on blood pressure that has been measured under different conditions for measurement is further provided.

Preferably, a selection requesting portion for presenting a selection request to a patient by prompting the patient to select predetermined conditions for measurement using the selection portion before the start of measurement of blood pressure by the blood pressure measuring portion is provided.

In order to achieve the above described object, an electronic blood pressure monitor according to another aspect of this invention is provided with: a blood pressure measuring portion having a cuff that is attached to the part where blood pressure is measured, a pressurizing and depressurizing portion for adjusting pressure that is applied to the cuff, a pressure detecting portion for detecting pressure within the cuff that is adjusted by the pressurizing and depressurizing portion, and a blood pressure calculating portion for calculating blood pressure on the basis of the pressure that is detected by the pressure detecting portion; a memory portion for storing data on blood pressure that is outputted from the blood pressure calculating portion; and a display portion for displaying at least the data on blood pressure. In addition, the electronic blood pressure monitor is further provided with: a selection portion for selecting predetermined conditions for measurement from among a number of types of conditions for measurement; a selection requesting portion for presenting a selection request to a patient by prompting the patient to select predetermined conditions for measurement using a selection portion before the start of measurement of blood pressure by the blood pressure measuring portion; and a data storing portion for linking data on blood pressure that has been outputted from the blood pressure calculating portion to the predetermined conditions for measurement that have been selected by the selection portion and storing the data on blood pressure and the predetermined conditions for measurement in the memory portion.

Preferably, the selection requesting portion displays a message in the display portion for prompting the patient to select predetermined conditions for measurement using the selection portion as the selection request.

Preferably, the selection requesting portion outputs a message in speech sound for prompting the patient to select predetermined conditions for measurement using the selection portion as the selection request.

Preferably, the selection requesting portion shows the selection portion in a predetermined manner using light as a selection request.

In order to achieve the above described object, a blood pressure measuring system according to still another aspect of this invention is provided with an electronic blood pressure monitor and an information processing apparatus. The electronic blood pressure monitor is provided with: a cuff that is attached to the part where blood pressure is measured; a blood pressure measuring portion having a pressurizing and depressurizing portion for adjusting pressure that is applied to the cuff, a pressure detecting portion for detecting pressure within the cuff that is adjusted by the pressurizing and depressurizing portion, and a blood pressure calculating portion for calculating blood pressure on the basis of the pressure that is detected by the pressure detecting portion; a memory portion for storing data on blood pressure that is outputted from the blood pressure calculating portion; and a display portion for displaying at least the data on blood pressure.

The electronic blood pressure monitor is further provided with: a selection portion for selecting predetermined conditions for measurement from among a number of types of conditions for measurement before the start of measurement of blood pressure by the blood pressure measuring portion; a control portion for starting measurement of blood pressure by the blood pressure measuring portion; and a data storing portion for linking data on blood pressure that has been outputted from the blood pressure calculating portion to the predetermined conditions for measurement that have been selected by the above described selection portion and storing the data on blood pressure and the predetermined conditions for measurement in the memory portion.

The information processing apparatus is provided with an information generating portion for receiving the content that is stored in the memory portion from the electronic blood pressure monitor and generating blood pressure management information on the basis of the received content; and an information displaying portion for displaying the above described blood pressure management information that has been generated by the information generating portion.

According to this invention, the configuration of the electronic blood pressure monitor is provided with a selection portion for selecting predetermined conditions for measurement from among a number of types of conditions for measurement, such as after waking up, before sleeping, normal and the like, and when predetermined conditions for measurement are selected in the selection portion, measurement is started in accordance with this selection operation, and the data on measured blood pressure is automatically stored in the memory portion that is linked to the selected predetermined conditions for measurement so as to be managed.

In addition, selection of the conditions for measurement is also used as an instruction of the start of measurement, and thus, it is not necessary to input conditions for measurement separately for every measurement, and therefore, input of the conditions for measurement can be prevented from being forgotten, and incorrect input of the conditions for measurement can also be prevented.

In addition, an evaluation amount is calculated on the basis of the mutual relationship between a group of data on blood pressure that has been measured under the same conditions for measurement, which are stored in the memory portion as described above, and a group of data on blood pressure that has been measured under different conditions for measurement, and therefore, miscalculation of the evaluation amount caused by incorrect linkage of the measurement results to the conditions for measurement due to incorrect setting of the clock inside the electronic blood pressure monitor can be prevented.

In addition, it is possible for a patient to set conditions for measurement (such as after waking up, before sleeping and the like) which are appropriate for his/her life cycle via the selection portion in the case where types of conditions for measurement, such as after waking up, before sleeping, normal and the like, are provided, and therefore, even those such as shift workers, whose life cycle, including the time for waking up and sleeping, is different from ordinary people, can use data on blood pressure and the conditions for measurement which are linked to and stored in the memory portion, so that the evaluation value which correctly reflects the life cycle of the patient can be calculated.

In addition, it becomes unnecessary to separately input conditions for measurement for every measurement, as described above, and therefore, input of conditions for measurement can be prevented from being forgotten and incorrect input of conditions for measurement can also be prevented, and as a result, the evaluation amount can be prevented from being miscalculated.

In addition, generation and display of blood pressure management information that includes the above described evaluation amount can provide a system in an external information processing apparatus of the electronic blood pressure monitor.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

In the following, the embodiments of this invention are described in detail in reference to the drawings. In the following descriptions, the same symbols are attached to parts and components that are the same. The names and functions of these are also the same. Accordingly, detailed descriptions for these are not repeated.

(Configuration)

Figure 1:
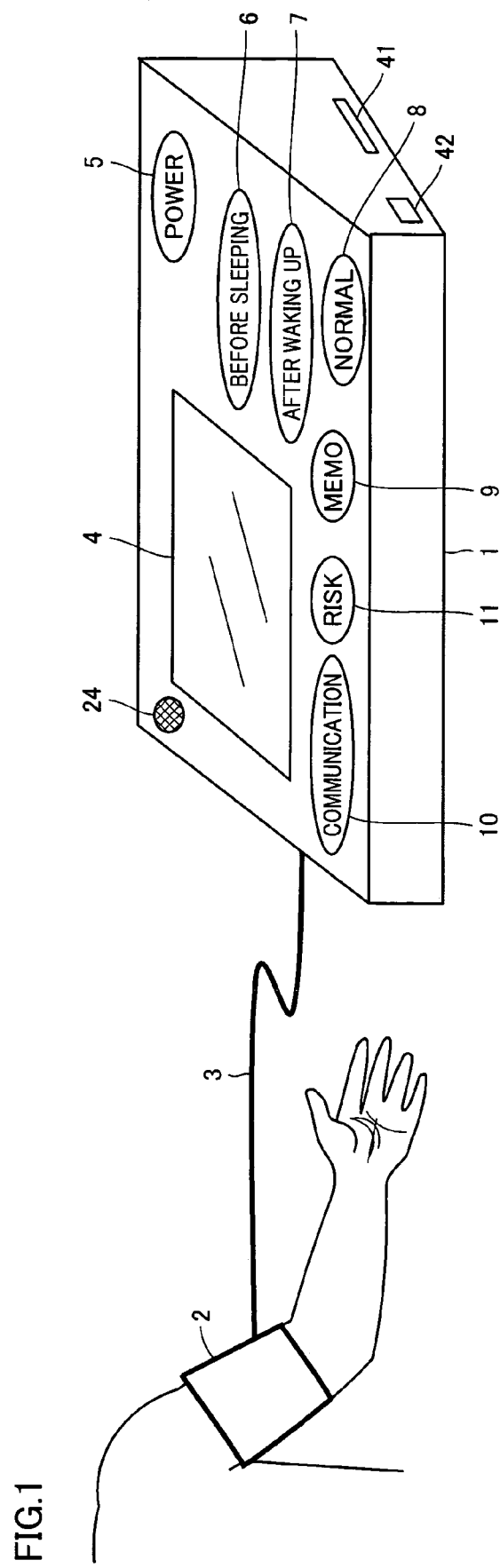
FIG. 1 is a schematic diagram of an electronic blood pressure monitor according to the present embodiment.

In reference to FIG. 1, an electronic blood pressure monitor according to the present embodiment is provided with a blood pressure monitor main body 1, a cuff 2 for applying pressure by means of air pressure which is attached to the part of a patient where blood pressure is measured, and an air tube 3 for connecting blood pressure monitor main body 1 to cuff 2.

Blood pressure monitor main body 1 has a display portion 4 that is provided so that a patient can confirm the content of display, a power switch 5, measurement switches 6, 7 and 8, a memo switch 9, a communication switch 10 and a risk display switch 11 that are provided so that a patient can externally operate the blood pressure monitor, a speaker 24, a recording medium attachment portion 41 through which a recording medium can be attached to blood pressure monitor main body 1 from the outside so as to be freely removable, and a communication connector portion 42 to which a cable (not shown) for allowing blood pressure monitor main body 1 to communicate with an external apparatus is attached so as to be freely removable.

Power switch 5 is operated in order to turn on/off the power supply of blood pressure monitor main body 1. Measurement switches 6, 7 and 8 are respectively operated in order to instruct the start of measurement of blood pressure; measurement switch 6 is operated in the case where measurement of blood pressure is carried out before sleeping, for example, within two hours before sleeping, measurement switch 7 is operated in the case where the measurement of blood pressure is carried out after waking up, for example, within two hours after waking up, and measurement switch 8 is operated when blood pressure is measured in other cases. Letters that read "before sleeping," "after waking up" and "normal" are printed on measurement switches 6, 7 and 8, respectively.

Memo switch 9 is operated in the case where measurement of blood pressure is carried out in specific situations. In the case where, for example, a patient is instructed by a doctor to measure blood pressure after taking a prescribed medicine, memo switch 9 is operated when blood pressure is measured when the patient has forgotten to take the medicine, and thereby, the results of measurement are recorded with added information that indicates that the results of measurement were gained without the patient taking the medicine. This correspondence is described in detail below.

Communication switch 10 is operated in the case where the data on the results of measurement by blood pressure monitor main body 1 is transmitted through a communication system to an external apparatus. Risk display switch 11 is operated in order to display information on cardiovascular risk on the basis of the data on the results of measurement by blood pressure monitor main body 1 on display portion 4.

Figure 2:
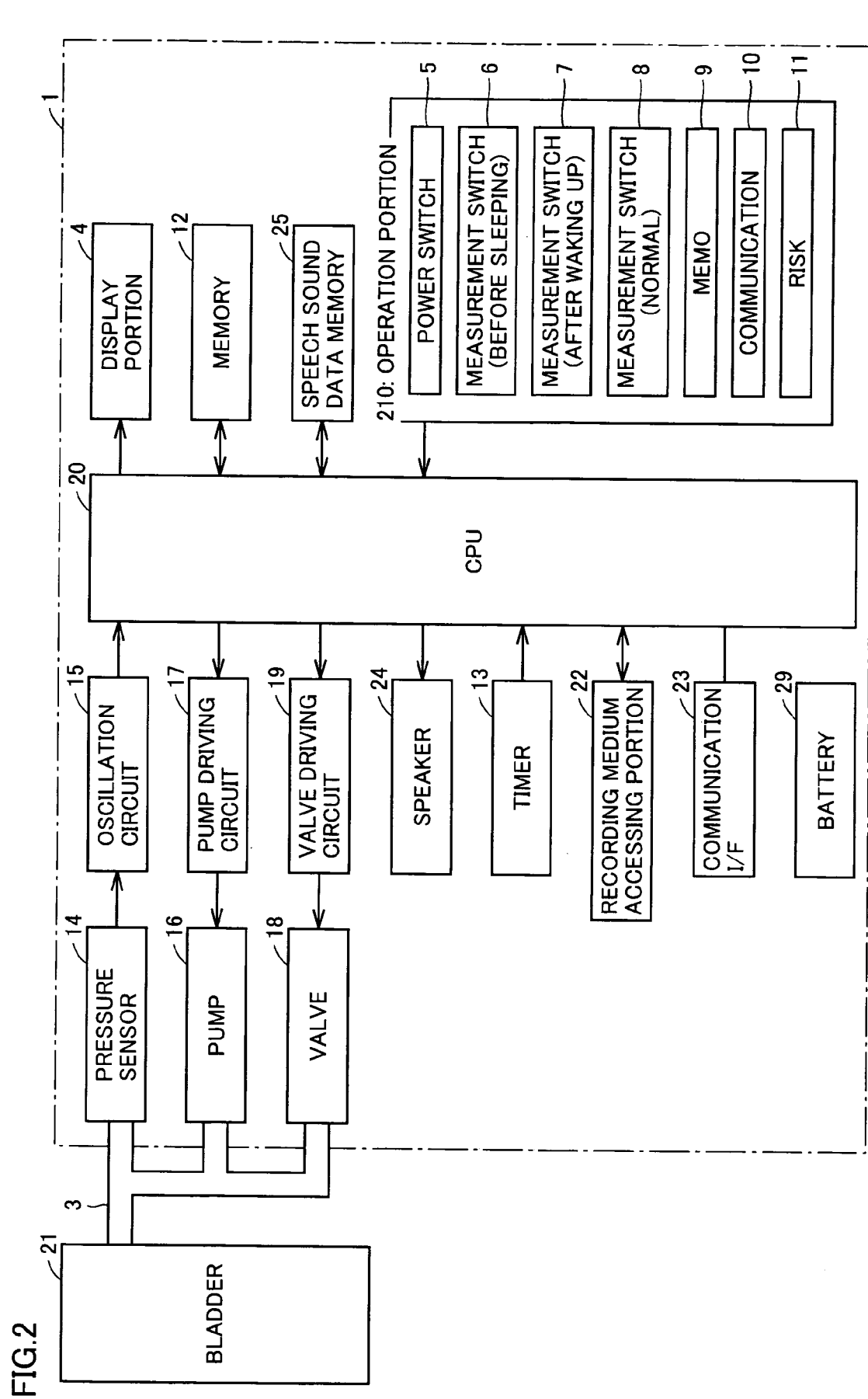
FIG. 2 is a diagram showing an example of the internal configuration of an electronic blood pressure monitor according to the present embodiment.

FIG. 2 shows the internal configuration of blood pressure monitor main body 1. In reference to FIG. 2, blood pressure monitor main body 1 includes a pressure sensor 14 for outputting a change in the pulse pressure of the part to be measured that is detected via a bladder 21, which is an air bag that is incorporated in cuff 2 as a pulse wave signal, an oscillation circuit 15 for outputting a pulse signal having a period corresponding to a voltage signal that indicates the pulse wave signal that is outputted from pressure sensor 14, a pump 16 and a valve 18 for adjusting the level of application of pressure (air pressure) by means of bladder 21, a pump driving circuit 17 for driving pump 16, a valve driving circuit 19 for adjusting the opening and closing of valve 18, a display portion 4, a memory 12, an operation portion 210, a timer 13 which operates to measure time and outputs measured time data, a recording medium accessing portion 22, a communication I/F (abbreviation for interface) 23, a speaker 24, a speech sound data memory 25, a battery 29 and a CPU (central processing unit) 20 for controlling each of these portions. Bladder 21 is connected to pressure sensor 14, pump 16 and valve 18 via an air tube 3. Here, though power for driving each portion is supplied from battery 29, it may be supplied from a commercial power supply. CPU 20 calculates the blood pressure value, the pulse rate and the like on the basis of the pulse signal that is inputted from oscillation circuit 15.

Operation portion 210 has power switch 5, measurement switches 6, 7 and 8, memo switch 9, communication switch 10 and risk display switch 11, as shown in FIG. 1.

Recording medium accessing portion 22 reads out data from or writes data into a recording medium that has been attached through recording medium attachment portion 41 under the control of CPU 20. Communication I/F 23 communicates with an external apparatus via a cable that is connected to communication connector portion 42 under the control of CPU 20.

A variety of types of programs and data for controlling data on the results of measurement, the blood pressure measuring operation, the displaying operation via display portion 4, the communication operation and the like are stored in memory 12.

In the above described configuration, at the time of measurement of blood pressure, CPU 20 converts a pulse signal (pressure signal) that has been outputted form oscillation circuit 15 into digital data, and after that, applies a predetermined algorithm on this data so as to determine the systolic blood pressure and the diastolic blood pressure, and at the same time, calculate the pulse rate. A conventional, known procedure can be applied to such a procedure for measurement, and therefore, here, the detailed description thereof is omitted.

Figure 3B:
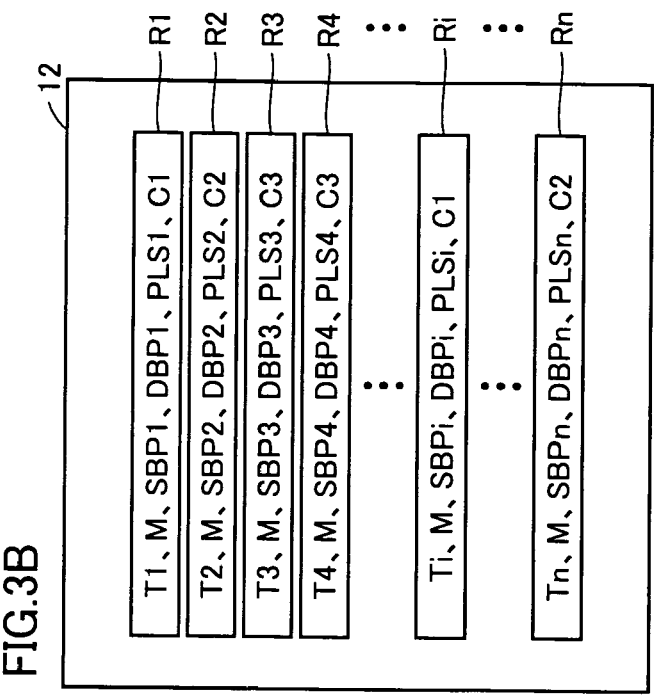
FIGS. 3A and 3B are diagrams showing examples of the content stored in a memory.
Figure 3A:
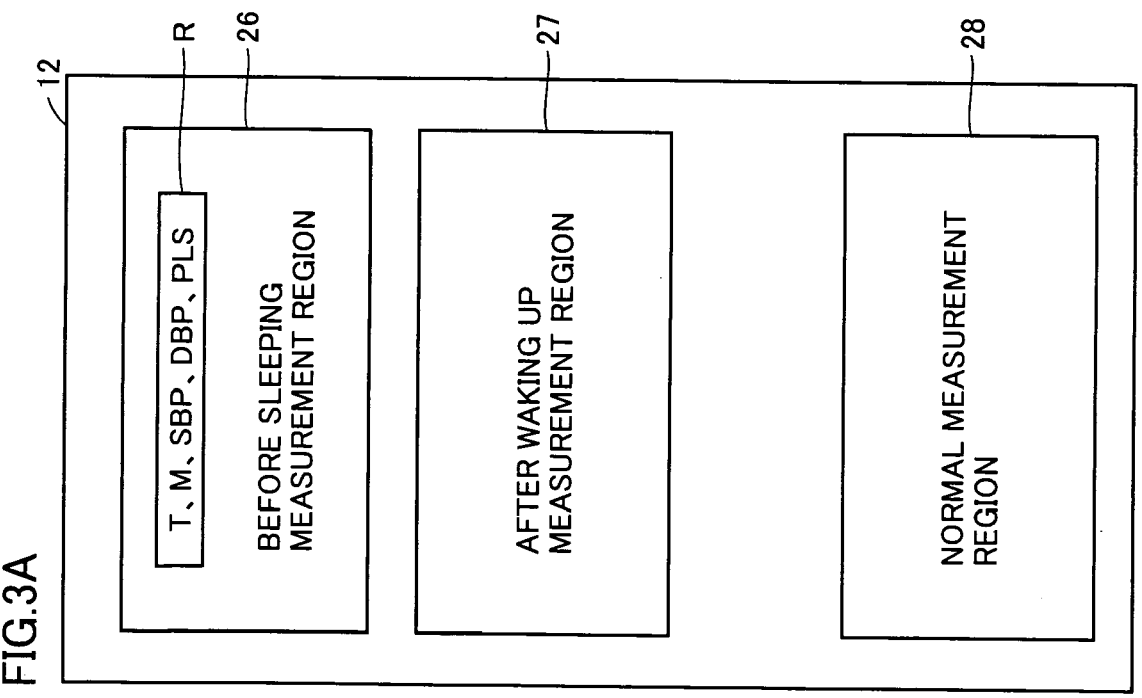

As shown in FIGS. 1 and 2, the electronic blood pressure monitor according to the present embodiment is provided with a number of measurement start switches 6, 7 and 8, which are operation switches for instructing the start of measurement of blood pressure, in such a manner that conditions for measurement which are sections time slots for measurement in accordance with the life rhythm (before sleeping, after waking up, normal) are allocated to the respective measurement start switches in advance, and the results of measurement are linked to the conditions for measurement which are indicated by the switch that has been operated for instructing the start of measurement of blood pressure, and are stored in a predetermined region of memory 12. As described above, in the electronic blood pressure monitor according to the present embodiment, switches for instructing the start of measurement and switches for selecting the conditions for measurement are shared. FIGS. 3A and 3B show examples of the results of measurement that have been stored in memory 12 in the case where blood pressure is measured through switching operations, as described above.

As a concrete example of corresponding storage, as shown in FIG. 3A, a method can be cited, where the results of measurement are sorted into groups on the basis of information on the conditions for measurement that correspond to the measurement start switch that is operated for starting measurement, that is to say, on the basis of the section in the time slot for measurement, that is, any of before sleeping, after waking up and normal, so as to be stored in regions 26, 27 and 28 for each group in memory 12. The results of measurement are respectively stored in regions 26, 27 and 28 in a record R unit. Record R includes measurement time data T, memo flag M, systolic blood pressure data SBP, which indicates the systolic blood pressure, diastolic blood pressure DBP, which indicates the diastolic blood pressure, and pulse rate data PLS, which indicates the pulse rate. These pieces of data may be made to correspond to the conditions for measurement for every measurement and stored in the respective regions, but the present invention is not limited to the storage format using record R.

As for measurement time data T, the data on the measured time (time when measurement is started or completed) that is measured by timer 13 is inputted into CPU 20 and stored in record R. Memory flag M indicates either 0 or 1. CPU 20 detects whether or not memo switch 9 is operated in the case of measurement of blood pressure, and sets the value of memo flag M of record R of the results of this measurement. Concretely, in the case where memo switch 9 is operated, memo flag M of this record R is set to 1, and in the case where it is not operated, it is set to 0.

In the following description, as shown in FIG. 3A, it is assumed that blood pressure values are sorted into groups on the basis of information on the conditions for measurement and stored in the respective memory regions, and the method for linking the data to the conditions for measurement is, of course, not limited to this method. For example, as shown in FIG. 3B, a method for making pairs of blood pressure value and information on the conditions for measurement and storing the pairs in memory 12 may be used. In FIG. 3B, records Ri (i=1, 2, 3, . . . , n), where blood pressure values and information on the conditions are paired and stored, are stored in memory 12 for each measurement of blood pressure. Measurement time data Ti, systolic blood pressure data SBPi, diastolic blood pressure data DBPi, pulse rate data PLSi and any of measurement condition data C1, C2 and C3 are stored in record Ri. Measurement condition data C1, C2 and C3 correspond to information on the conditions for measurement which corresponds to the measurement start switch that has been operated for starting the measurement, that is to say, sections of the time slots for measurement; before sleeping, after waking up and normal, respectively.

(Calculation of Risk Value)

In the present embodiment, cardiovascular risk is calculated on the basis of the blood pressure values that have been measured and stored in memory 12. Concretely, CPU 20 calculates risk values on the basis of a program for calculating the cardiovascular risk value that has been stored in an internal memory or memory 12 in advance. In order to calculate the risk value, first, CPU 20 reads out the blood pressure values that have been stored in memory 12, and carries out a process for calculating the average of the blood pressure values for each of regions 26, 27 and 28 shown in FIG. 3A. That is to say, the group average of blood pressure data groups that include blood pressure data which has been measured under the same conditions for measurement is calculated for each blood pressure data group. Thus, the risk value is calculated using the average blood pressure value that has been calculated within a blood pressure data group.

Calculation of the average blood pressure value is carried out using the following equations.

average of measurement after waking up SBP=(result of measurement after waking up SBP1+ result of measurement after waking up SBP2+ . . . +result of measurement after waking up SBP$n$)/$n$ (here, $n$=1, 2, 3, . . . )

average of measurement before sleeping SBP=(result of measurement before sleeping SBP1+result of measurement before sleeping SBP2+ . . . +result of measurement before sleeping SBP$m$)/$m$ (here, $m$=1, 2, 3, . . . )

In addition, in order to calculate the risk value, the average values (ME average values) of blood pressure values that have been measured in the time slot before sleeping and the time slot after waking up, and the difference between the two (ME difference), which are calculated in accordance with the following equations, are used.

ME difference=average of measurement after waking up SBP−average of measurement before sleeping SBP ME average=(average of measurement after waking up SBP+average of measurement before sleeping SBP)/2

Calculation of these risk values is particularly effective for preventing cardiovascular problems, such as cerebral strokes, heart failure, cerebral infarction, cerebral hemorrhage, subarachnoid hemorrhage, transient cerebral ischemic attack, falling, fainting, vertigo, tottering, myocardial infarction, angina pectoris, asymptomatic myocardial ischemia, arrhythmia, sudden death, dissecting aortic aneurism and ruptured aortic aneurism.

Blood pressure varies on the basis of a variety of factors, and therefore, measurement of blood pressure is preferably repeated in these time slots over a number of days, so that the average value can be found for each time slot, and then, the ME average value and the ME difference can be gained and the results found, and thus, the precision of risk analysis becomes higher.

In the electronic blood pressure monitor according to the present invention, a risk analysis process is carried out in accordance with the calculated risk value, and therefore, groups of blood pressure data, each of which includes at least one blood pressure value that is respectively measured in the time slot before sleeping and in the time slot after waking up (data that is included in before sleeping region 26 and after waking up region 27) is gained, so that the average of blood pressure values that are included in each group is calculated, and after that, two risk values of diseases of the cardiovascular system, the average value (ME average value) and the difference (ME difference) between the groups, are calculated, and then, these risk values are proposed (displayed) as the results. The results of the risk values may be proposed as the ME average value and the ME difference, as described above, and in addition, may be outputted in the method shown in FIG. 4 of Japanese Patent Laying-Open No. 2004-261452.

(Measurement Procedure)

In the electronic blood pressure monitor of the present embodiment, as shown in FIG. 1, a number of measurement start switches which are operated in order to instruct the start of measurement of blood pressure are provided for each type of condition for measurement.

Figure 4:
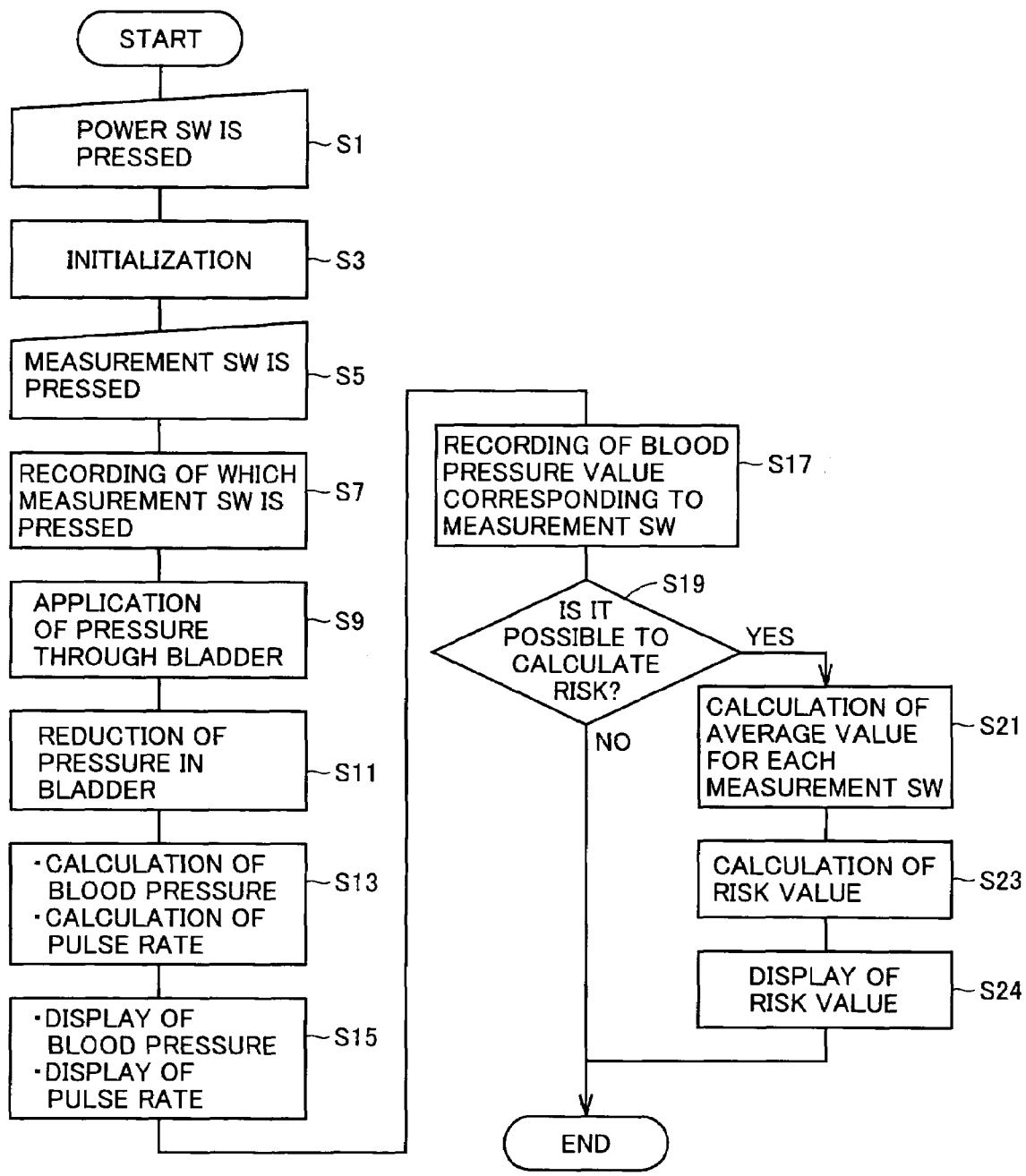
FIG. 4 is a flow chart of a process according to the present embodiment.

A blood pressure measuring operation following the flow chart of FIG. 4 is described below. The flow chart of FIG. 4 has been stored in memory 12 in advance as a program, and is read out and executed by CPU 20.

First, when the patient puts cuff 2 around the part to be measured and operates power switch 5 of the electronic blood pressure monitor, an operation signal is sent to CPU 20, and therefore, CPU 20 starts making battery 29 supply power to each portion on the basis of the operation signal (Step S(hereinafter simply referred to as S)1). Next, CPU 20 controls each portion as an initialization process for the electronic blood pressure monitor so as to exhaust the air within bladder 21 and correct pressure sensor 14 to 0 mmHg (S3).

Next, when the patient operates any of the measurement start switches in accordance with the conditions for measurement, that is to say, any of before sleeping switch 6, after waking up switch 7 and normal switch 8 (S5), an operation signal which is different for each of the operated switches is sent from operation portion 210 to CPU 20. CPU 20 determines which switch has been operated on the basis of the sent operation signal and temporarily records the data of the conditions for measurement that correspond to the switch that is indicated by the determination results in an internal memory (S7). In addition, present time data that is measured by timer 13 at this time is inputted and temporarily recorded in the internal memory as measured time data T.

Determination of the conditions for measurement on the basis of an operation switch is carried out, for example, in the following manner. That is to say, for each switch that is provided in operation portion 210, data on the operation signal which indicates that this switch has been operated is linked to the data on the instruction content that is indicated by this operation signal, and these pieces of data are stored in memory 12. Accordingly, this corresponding data is retrieved on the basis of the operation signal, so that data on the corresponding instruction content can be read out. Then, the read out data on the instruction content is interpreted, and thereby, it can be determined whether or not the conditions for measurement are provided, as well as which type of condition for measurement has been provided (before sleeping measurement, after waking up measurement or normal).

In accordance with the operation of the above described measurement start switches, CPU 20 controls each portion so as to apply pressure of up to approximately the systolic blood pressure of the patient+40 mmHg (S9), and after that, the pressure within bladder 21 is gradually reduced (S11). During this pressure reducing process, the pressure within bladder 21 is detected by pressure sensor 14, and CPU 20 calculates blood pressure (systolic blood pressure and diastolic blood pressure) values and the pulse rate on the basis of the detected pressure (S13), and then, displays the calculated blood pressure values and the pulse rate on display portion 4 (S15). The process for measuring blood pressure in S9 to S15 is the same as that of conventional electronic blood pressure monitors. Here, though measurement of blood pressure is carried out during the pressure reducing process, it may be carried out during the pressure increasing process.

When calculation and displaying of blood pressure is completed, CPU 20 registers a new record R where the results of the measurement (blood pressure values and pulse rate) and measured time data T have been stored in the region of memory 12 which corresponds to the data on the conditions for measurement that is indicated by the measurement start switch that was operated in S5 (S17).

After that, CPU 20 determines whether or not the number of risk values that can be calculated, for example, at least one or more, have been recorded as data in each region of memory 12 (S19), and in the case where it is determined that it is not recorded (NO in S19), the sequence of processes is completed, while in the case where it is determined that the number of risk values that can be calculated has been recorded as data in each region (YES in S19), the average value of the data group in each region is calculated in accordance with the above described procedure (S21). Then, the ME average value and the ME difference are calculated as the risk values of diseases of the cardiovascular system (S23), so that the calculated risk values are displayed on display portion 4 (S24).

(Another Embodiment)

Figure 5:
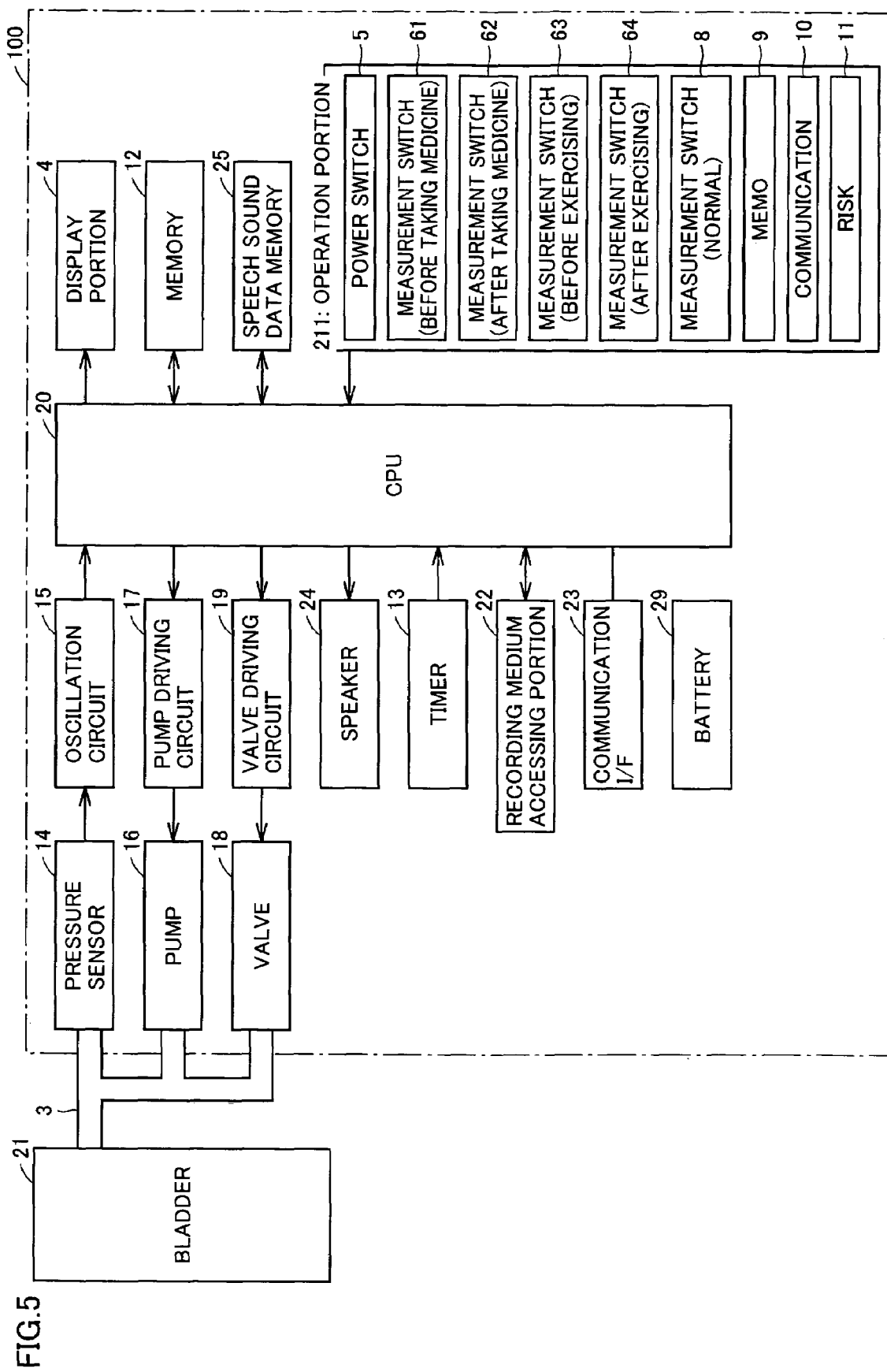
FIG. 5 is a diagram showing another example of the internal configuration of an electronic blood pressure monitor according to the present embodiment.

Regarding the types of conditions for measurement, though in the embodiment that is described in reference to FIG. 1, before sleeping, after waking up and normal are provided so as to correspond to the life rhythm, the types and the number thereof are not limited to this. As shown in FIG. 5, for example, conditions for measurement such as before taking medicine, after taking medicine, before exercising and after exercising may be provided.

Blood pressure monitor main body 100 of the electronic blood pressure monitor of FIG. 5 is provided with an operation portion 211 in place of operation portion 210 of blood pressure monitor main body 1 of FIG. 1, and the other parts of the configuration are the same as those of FIG. 1. Operation portion 211 has switches 61 to 64 which are operated as measurement starting switches in accordance with the conditions for measurement in place of before sleeping switch 6 and after waking up switch 7 of operation portion 210. Concretely, operation portion 211 has a before taking medicine switch 61 which is operated before taking medicine, an after taking medicine switch 62 which is operated after taking medicine, a before exercising switch 63 which is operated before exercising, and an after exercising switch 64 which is operated after exercising. The other switches of operation portion 211 are the same as those of operation portion 210.

Figure 6:
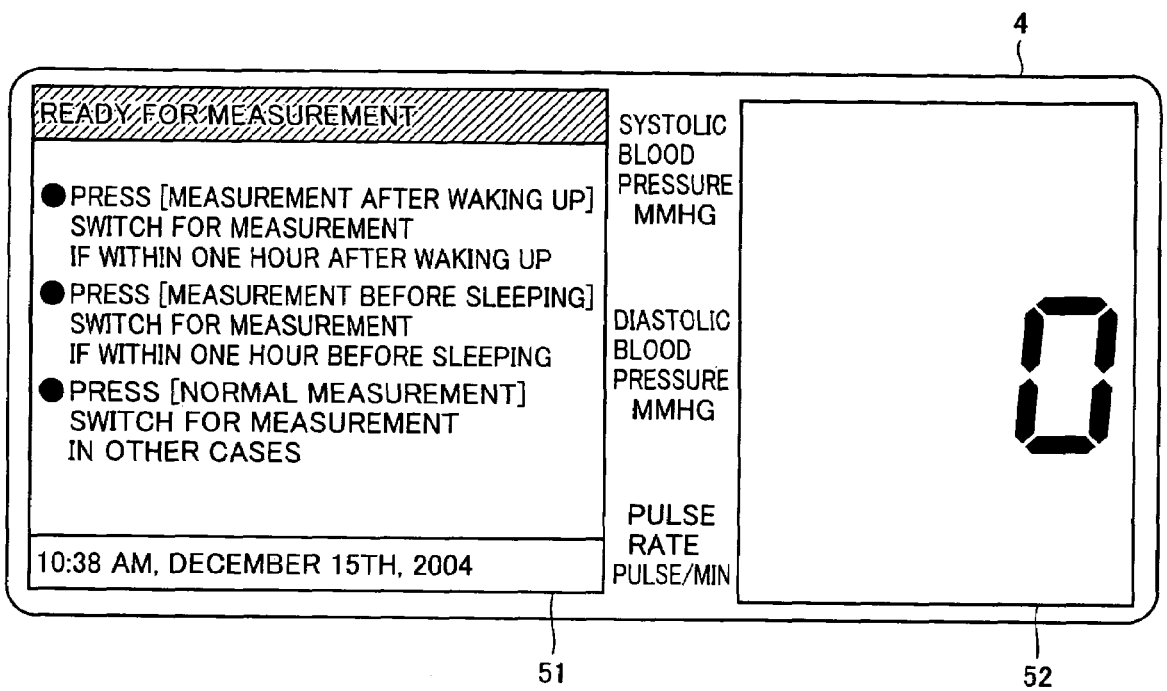
FIG. 6 is a diagram showing an example of a display according to the present embodiment.

In the procedure of FIG. 4, though it is assumed that a patient knows that measurement is started by operating a measurement starting switch which corresponds to the conditions for measurement subsequently to the operation of power switch 9, there may be some patients who don't know this. Accordingly, the patient may be concretely informed to the effect that measurement of blood pressure is started by operating a measurement starting switch. For example, CPU 20 may display a message as that shown in FIG. 6 on display portion 4 after the completion of initiation (S3). In FIG. 6, display portion 4 has windows 51 and 52, and the patient is informed of the correspondence between the conditions for measurement and the measurement switches of operation portion 210 to be operated through a message in window 51. This message functions as a message for selection request for prompting the patient so that the patient selects specific conditions for measurement before the start of measurement. Window 52 displays the results of measurement. The patient checks the message on window 51, and thereby, can easily specify the measurement starting switch for instructing the start of measurement.

In addition, a message for selection request as that shown in FIG. 6 may be provided in speech sound. Concretely, speech sound data of the message of FIG. 6 may be stored in speech sound data memory 25 in advance, so that CPU 20 reads out this speech sound data and outputs it from speaker 24 as speech sound after data conversion.

Alternatively, LED's (Light Emitting Diodes) or the like may be incorporated in measurement switches 6, 7 and 8, so that the measurement starting switch to be operated next is shown by making these LED's light up in a predetermined mode (blinking, continuous or the like).

In addition, two or more from among message display, speech sound output and turning on of switches may be combined, and thereby, the patient may be informed to the effect that measurement of blood pressure has started through the operation of a measurement starting switch.

In addition, in the case where memo switch 9 is operated, operation is timed to coincide with any of S5 to S15. In the case where memo switch 9 is operated, CPU 20 temporarily records a memo flag M that has been set to "1," and this memory flag M is made to correspond to the results of measurement in S17 and recorded in memory 12. In addition, in the case where memo switch 9 is operated, this may be displayed together with the results of measurement in S15. In addition, in the case where the results of measurement on the basis of which the risk value has been calculated include the results of measurement when memory switch 9 is operated in S23, this may be displayed together with the risk value in S24.

In addition, though in the present embodiment, a process for risk value calculation/display is implemented through a sequence of operations starting from measurement of blood pressure, the process may be carried out only when required. That is to say, the processes of S19 to S24 may be carried out only in the case where the patient operates a risk display switch 11 after the recording in S17.

According to another embodiment, a blood pressure measuring system is provided with an electronic blood pressure monitor as that shown in the above described embodiment, as well as an information processing apparatus.

Figure 7:
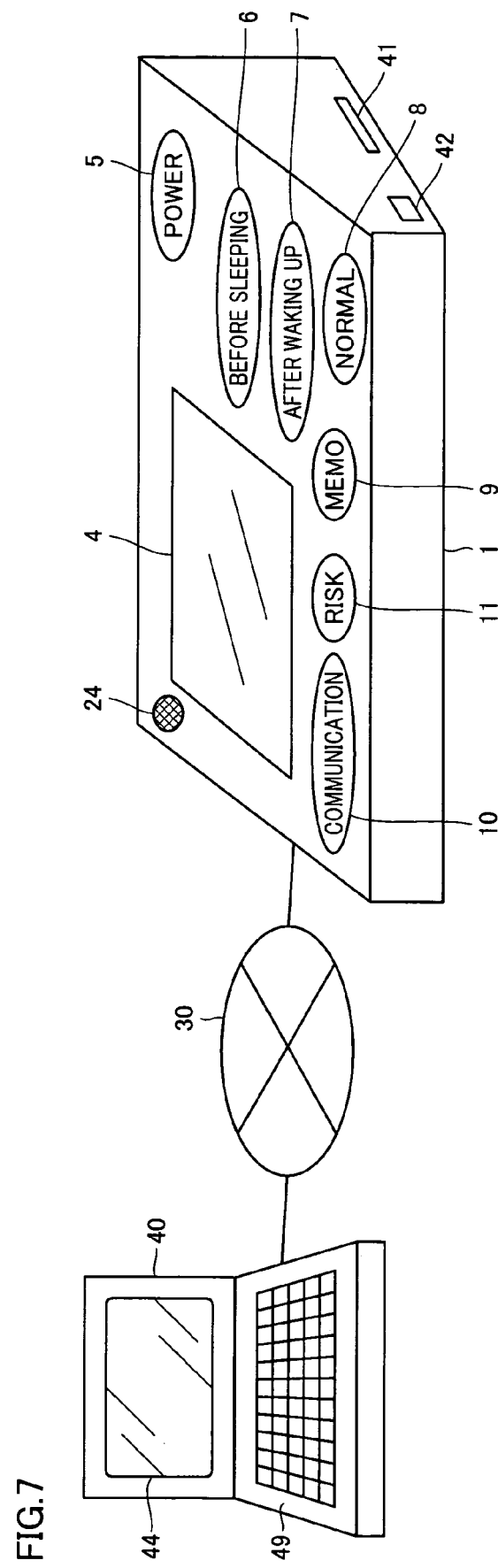
FIG. 7 is a diagram showing an example of the configuration of a system according to another embodiment.

In this system, the function of calculating the average value of each data group so as to calculate and display the risk value can be implemented, not with the electronic blood pressure monitor but with a personal computer which is an external information processing apparatus. For example, as shown in FIG. 7, an external personal computer 40 is provided with a function for calculating the average value of each data group that has been read out from memory 12 of the electronic blood pressure monitor, so as to calculate and display the risk value. The electronic blood pressure monitor and personal computer 40 are connected to each other through a communication line 30. The electronic blood pressure monitor becomes of a state where communication is possible using a communication I/F 23 and a communication connector portion 42, and when a patient operates communication switch 10 in this state, CPU 20 reads out data in regions 26 to 28 that has been stored in memory 12, and transfers the data to personal computer 40 via communication I/F 23 and communication line 3. Here, as communication line 30, a dedicated line, such as a local area network, or a public line, such as a telephone line, can be used.

Figure 8:
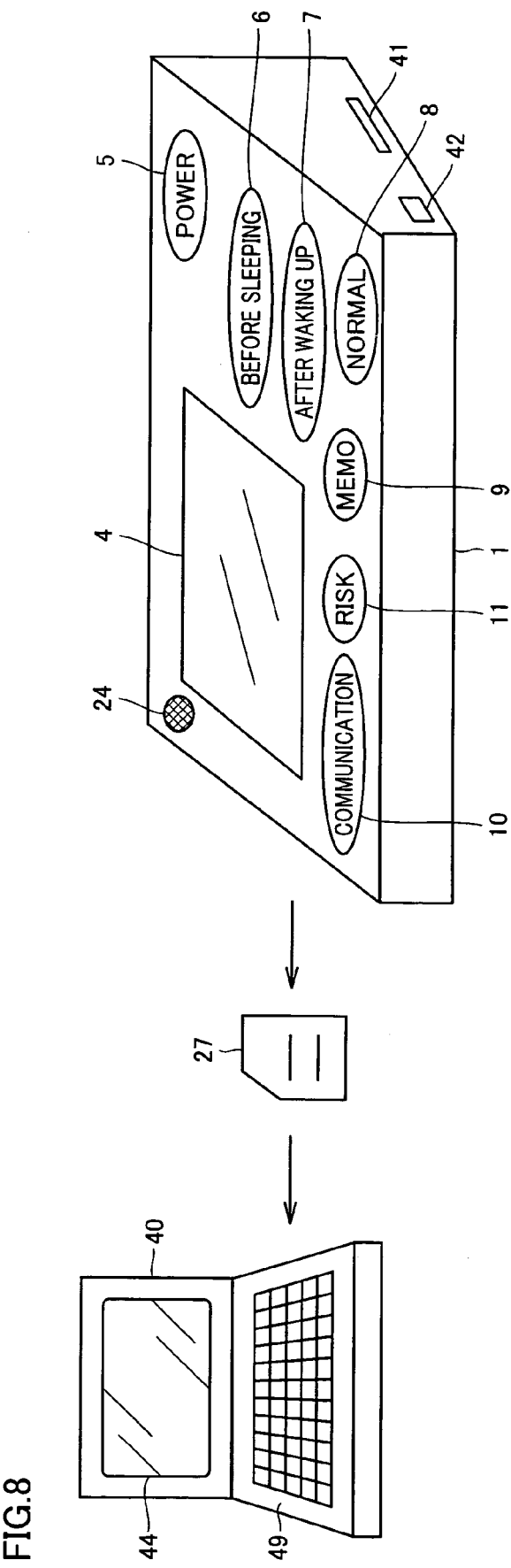
FIG. 8 is a diagram showing another example of the configuration of a system according to another embodiment.

In addition, delivery and reception of measured data may be carried out using a recording medium 27, which may be, for example, a memory card, as shown in FIG. 8, instead of data transfer via communication line 30 of FIG. 7. Concretely, recording medium 27 is attached to recording medium accessing portion 22, and CPU 20 reads out data in regions 26 to 28 of memory 12, and writes the data into recording medium 27 that has been attached through recording medium accessing portion 22. After writing in, recording medium 27 is removed and attached to personal computer 40, so that data can be read out, and thereby, transfer is carried out. In the case where recording medium 27 is attached through recording medium accessing portion 22, the results of measurement in S17 of FIG. 4 may be stored in recording medium 27 instead of in memory 12.

In addition, personal computer 40 may generate and display the blood pressure management information of a patient. This blood pressure management information includes the average value of the systolic blood pressure, the average value of the diastolic blood pressure, the average value of the pulse rate and the like per month unit for each data group that has been read out from memory 12, in addition to the above described risk value that has been calculated. On the display, the average value of the systolic blood pressure, the average value of the diastolic blood pressure and the average value of the pulse rate per month unit, which have been generated, may be linked to predetermined indices (appropriate blood pressure value, appropriate pulse rate) that have been provided by WHO (World Health Organization) when displayed.

Figure 9:
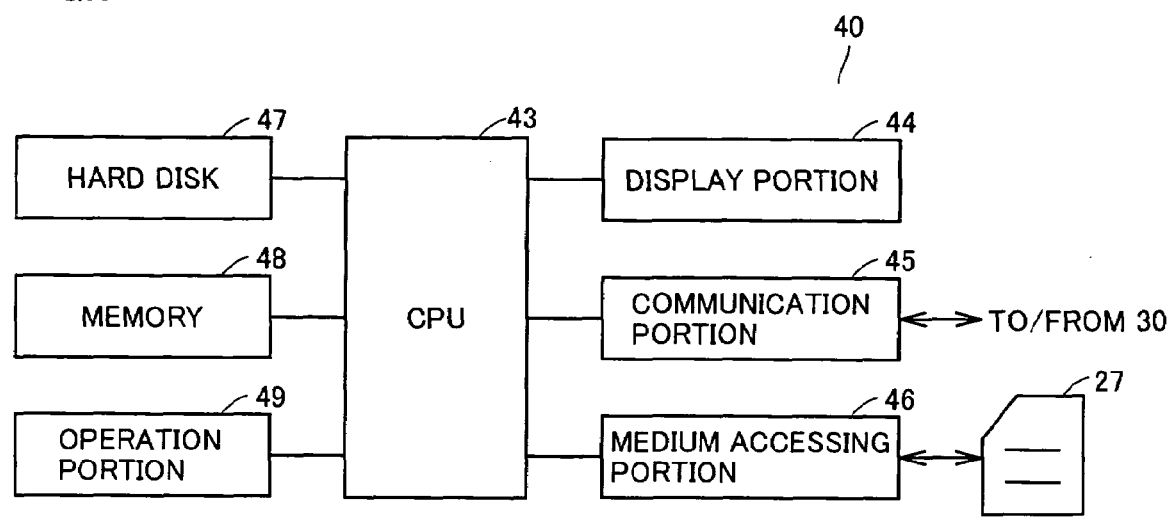
FIG. 9 is a diagram showing the configuration of a personal computer according to another embodiment.

In reference to FIG. 9, personal computer 40 is provided with a CPU 43, a display portion 44, a communication portion 45 for communicating with an external apparatus that includes an electronic blood pressure monitor via a communication line 30, a medium accessing portion 46 to which a variety of types of media, such as recording medium 27, are attached so as to be freely removable, and which accesses the attached recording medium, a hard disk 47 for storing data and programs, a memory 48 made of a RAM (random access memory) or a ROM (read only memory) for storing data and programs, and an operation portion 49, such as a keyboard.

CPU 43 receives, via communication portion 45, data that has been transmitted from an electronic blood pressure monitor through communication line 30. In addition, CPU 43 receives data that has been read out from recording medium 27 that is attached to medium accessing portion 46. Data that is received or accepted by CPU 43 in this manner includes data on the results of blood pressure measurement that has been read out form memory 12 of an electronic blood pressure monitor.

CPU 43 reads out and implements a program for generating information that has been stored in memory 48 in advance, and thereby, the above described blood pressure management information is generated on the basis of the data on the results of blood pressure measurement that has been received or accepted. CPU 43 displays the generated blood pressure management information on display portion 44.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic blood pressure monitor, comprising:
   a blood pressure measuring portion;
   a memory portion for storing data on blood pressure that is measured by said blood pressure measuring portion;
   a display portion for displaying at least said data on blood pressure;
   a selection portion for selecting predetermined user conditions for measurement and triggering, upon selection, the start of measurement of blood pressure by said blood pressure measuring portion;
   a control portion for starting measurement of blood pressure by said blood pressure measuring portion in response to the selection of said predetermined user conditions for measurement by said selection portion; and
   a data storing portion for linking said data on blood pressure that has been measured to said predetermined user conditions for measurement that have been selected by said selection portion, and storing the data on blood pressure and the predetermined user conditions for measurement in said memory portion,
   said blood pressure measuring portion including
   a cuff that is attached to the part where blood pressure is measured,
   a pressurizing and depressurizing portion for adjusting pressure that is applied to said cuff,
   a pressure detecting portion for detecting pressure within said cuff that is adjusted by said pressurizing and depressurizing portion, and
   a blood pressure calculating portion for calculating blood pressure on the basis of the pressure that is detected by said pressure detecting portion,
   said selection portion comprising a plurality of switches, each switch corresponding to a predetermined user condition for measurement and configured so that operation of the switch triggers the start of measurement of blood pressure for said corresponding predetermined user condition for measurement.

2. The electronic blood pressure monitor according to claim 1, wherein each switch of said selection portion is externally operated for triggering the start of measurement.

3. The electronic blood pressure monitor according to claim 2, wherein
   said predetermined user conditions for measurement include conditions for measurement which indicate, respectively, measurement of blood pressure "after waking up" and "before sleeping."

4. The electronic blood pressure monitor according to claim 2, wherein
   said predetermined user conditions for measurement include conditions for measurement which indicate, respectively, measurement of blood pressure "before taking medicine," "after taking medicine," "before exercising" and "after exercising."

5. The electronic blood pressure monitor according to claim 1, wherein said data storing portion pairs said selected predetermined user conditions for measurement and said data on blood pressure for each measurement of blood pressure and stores the pair in said memory portion.

6. The electronic blood pressure monitor according to claim 1, wherein
   said memory portion is provided with a memory region for each of said predetermined user conditions for measurement,
   said data storing portion stores said data on blood pressure in said memory region that corresponds to said selected predetermined user conditions for measurement for each measurement of blood pressure.

7. The electronic blood pressure monitor according to claim 1, further comprising:
a portion for calculating an evaluation amount on the basis of the mutual relationship between a group of data on blood pressure that includes at least one piece of said data on blood pressure that has been measured under the same conditions for measurement, which are stored in said memory portion, and said group of data on blood pressure that has been measured under different conditions for measurement.

8. The electronic blood pressure monitor according to claim 1, further comprising:
a selection requesting portion for presenting a selection request to a patient by prompting the patient to select predetermined user conditions for measurement using said selection portion before the start of measurement of blood pressure by said blood pressure measuring portion is provided.

9. The electronic blood pressure monitor according to claim 8, wherein said selection requesting portion makes said display portion display a message for prompting the patient to select predetermined user conditions for measurement using said selection portion as said selection request.

10. The electronic blood pressure monitor according to claim 8, wherein said selection requesting portion outputs a message in speech sound for prompting the patient to select predetermined user conditions for measurement using said selection portion as said selection request.

11. The electronic blood pressure monitor according to claim 8, wherein said selection requesting portion shows said selection portion in a predetermined manner using light as said selection request.

12. An electronic blood pressure monitor, comprising:
a blood pressure measuring portion;
a memory portion for storing data on blood pressure that is measured by said blood pressure measuring portion;
a display portion for displaying at least said data on blood pressure;
a selection portion for selecting predetermined user conditions for measurement and triggering, upon selection, the start of measurement of blood pressure by said blood pressure measuring portion;
a selection requesting portion for presenting a selection request to a patient by prompting the patient to select predetermined user conditions for measurement using said selection portion before the start of measurement of blood pressure by said blood pressure measuring portion; and
a data storing portion for linking said data on blood pressure that has been measured to said predetermined user conditions for measurement that have been selected by said selection portion and storing the data on blood pressure and the predetermined user conditions for measurement in said memory portion,
said blood pressure measuring portion including
a cuff that is attached to the part where blood pressure is measured,
a pressurizing and depressurizing portion for adjusting pressure that is applied to said cuff,
a pressure detecting portion for detecting pressure within said cuff that is adjusted by said pressurizing and depressurizing portion, and
a blood pressure calculating portion for calculating blood pressure on the basis of the pressure that is detected by said pressure detecting portion,
said selection portion comprising a plurality of switches, each switch corresponding to a predetermined user condition for measurement and configured so that operation of the switch triggers the start of measurement of blood pressure for said corresponding predetermined user condition for measurement.

13. The electronic blood pressure monitor according to claim 12, wherein said selection requesting portion makes said display portion display a message for prompting the patient to select predetermined user conditions for measurement using said selection portion as said selection request.

14. The electronic blood pressure monitor according to claim 12, wherein said selection requesting portion outputs a message in speech sound for prompting the patient to select predetermined user conditions for measurement using said selection portion as said selection request.

15. The electronic blood pressure monitor according to claim 12, wherein said selection requesting portion shows said selection portion in a predetermined manner using light as said selection request.

16. A blood pressure measuring system, comprising an electronic blood pressure monitor and an information processing apparatus,
wherein said electronic blood pressure monitor includes:
a blood pressure measuring portion having
a cuff that is attached to the part where blood pressure is measured,
a pressurizing and depressurizing portion for adjusting pressure that is applied to said cuff,
a pressure detecting portion for detecting pressure within said cuff that is adjusted by said pressurizing and depressurizing portion, and
a blood pressure calculating portion for calculating blood pressure on the basis of the pressure that is detected by said pressure detecting portion;
a memory portion for storing data on blood pressure that is outputted from said blood pressure calculating portion;
a display portion for displaying at least said data on blood pressure;
a selection portion for selecting predetermined user conditions for measurement and triggering, upon selection, the start of measurement of blood pressure by said blood pressure measuring portion;
a control portion for starting measurement of blood pressure by said blood pressure measuring portion in response to the selection of said predetermined user conditions for measurement by said selection portion; and
a data storing portion for linking said data on blood pressure that has been outputted from said blood pressure calculating portion to said predetermined user conditions for measurement that have been selected by said selection portion and storing the data on blood pressure and the predetermined user conditions for measurement in said memory portion,
said selection portion comprising a plurality of switches, each switch corresponding to a predetermined user condition for measurement and configured so that operation of the switch triggers the start of measurement of blood pressure for said corresponding predetermined user condition for measurement, and said information processing apparatus includes:
an information generating portion for receiving the content that is stored in said memory portion from said electronic blood pressure monitor and generating blood pressure management information on the basis of the received content; and an information displaying portion for displaying said blood pressure management information that has been generated by said information generating portion.

* * * * *